United States Patent

Schmuck et al.

[11] Patent Number: 5,707,786
[45] Date of Patent: Jan. 13, 1998

[54] PROCESSING OF COLOR PHOTOGRAPHIC SILVER HALIDE MATERIALS

[75] Inventors: Arno Schmuck, Leichlingen; Jörg Hagemann, Köln; Norman Klaunzer, Leverkusen, all of Germany

[73] Assignee: Agfa-Gevaert, Leverkusen, Germany

[21] Appl. No.: 677,727

[22] Filed: Jul. 8, 1996

[30] Foreign Application Priority Data

Jul. 17, 1995 [DE] Germany ............... 195 25 968.8
Aug. 4, 1995 [DE] Germany ............... 195 28 777.0

[51] Int. Cl.$^6$ ............................... G03C 7/407
[52] U.S. Cl. .................... 430/373; 430/414; 430/435; 430/440; 430/446; 430/480; 430/483; 430/943
[58] Field of Search ................... 430/373, 414, 430/943, 435, 440, 446, 480, 483

[56] References Cited

U.S. PATENT DOCUMENTS

| | | | |
|---|---|---|---|
| 4,954,425 | 9/1990 | Iwano | 430/943 |
| 5,200,301 | 4/1993 | Wingender et al. | 430/373 |
| 5,358,830 | 10/1994 | Twist | 430/943 |
| 5,418,117 | 5/1995 | Marsden | 430/943 |
| 5,466,562 | 11/1995 | Marsden | 430/943 |

FOREIGN PATENT DOCUMENTS

| | | |
|---|---|---|
| 90/13061 | 11/1990 | WIPO. |
| 92/05471 | 4/1992 | WIPO. |
| 92/07302 | 4/1992 | WIPO. |
| 92/09009 | 5/1992 | WIPO. |

*Primary Examiner*—Hoa Van Le
*Attorney, Agent, or Firm*—Connolly & Hutz

[57] ABSTRACT

By means of a development intensification process for processing color photographic silver halide materials, the silver halide emulsions of which contain more than 90 mol. % of AgCl and less than 0.8 g of silver halide per m$^2$ (stated as the equivalent quantity of AgNO$_3$), short processing times accompanied by stable replenishment rates are obtained if at least one compound of the formulae (I), (II) or (III) is used as the developer substance in a quantity of 0.002 to 0.04 mol/l of developer solution

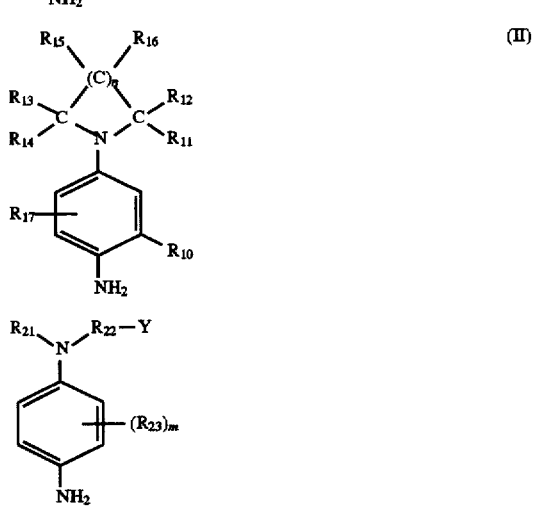

in which $R_1$ to $R_3$, $R_{10}$ to $R_{17}$, $R_{21}$ to $R_{23}$, m, n and Y have the meaning stated in the specification.

7 Claims, No Drawings

PROCESSING OF COLOR PHOTOGRAPHIC SILVER HALIDE MATERIALS

This invention relates to a novel variant of the development intensification process for processing of colour photographic silver halide materials exposed with an image, the silver halide emulsions of which contain more than 90 mol. % of AgCl and less than 0.8 g of silver halide per m² (stated as the equivalent quantity of AgNO₃).

Methods for intensifying silver images have long been known. In *History of Colour Photography* by Joseph S. Friedmann, Focal Press Ltd., London (1968), page 406 it is described that the oxygen formed by decomposition of peroxide on a silver image may be used in the presence of a paraphenylenediamine colour developer and a colour coupler to form a dye. DE 1 813 920 describes a method for the production of colour photographic images with paraphenylenediamines and catalytically decomposable peroxy compounds. Other photographic methods which exploit the decomposition of $H_2O_2$ on noble metal surfaces are described in DE 1 950 102, 1 961 029, 2 044 833, 2 044 993, 2 056 359 and 2 056 360.

Current methods for image intensification are, for example, intensification with peroxides in the presence of $Co^{3+}$ complexes as catalysts. Environmental disadvantages have prevented their introduction onto the market.

The greatest intensification factor and lowest fog are achieved on intensification of AgCl materials with $H_2O_2$. There are two methods which are suitable for intensification processing with silver chloride materials: the two bath process and the monobath process.

In the two bath process, the colour photographic material exposed with an image is immersed in a colour developer and then in a colour intensification bath which contains $H_2O_2$ or an $H_2O_2$ releasing compound.

In the monobath intensification process, the developer bath contains $H_2O_2$ or an $H_2O_2$ releasing compound as well as a paraphenylenediamine colour developer. Elevated intensification, even with materials having a low silver content, is achieved if the monobath contains less than $2 \times 10^{-4}$ mol/l of bromide or iodide. The disadvantage of the monobath intensification process is the low stability of the developer solution. WO 92/07302, WO 92/09009, EP 0 469 046 and WO 92/05471 describe processes which may improve the stability of the monobath process or of the developer solution.

Development times of between 30 and 60 s are achieved with the monobath colour intensification process.

Processing times of 20 s for development and of 5 s for the subsequent intensification are described in the two bath intensification process.

The object of the invention is to provide a development intensification process for processing colour photographic materials in which short processing times for development and intensification may be achieved. The process should also be distinguished by very stable processing conditions and very low replenishment rates and should also provide very light-stable colour images with low fog and elevated maximum density, even when materials containing little silver and low developer concentrations are used.

This object is achieved by using at least one colour developer of the formulae (I), (II) or (III) in a quantity of 0.002 to 0.04 mol/l of developer solution in a development intensification process.

The present invention accordingly provides a development intensification process for processing colour photographic silver halide materials, the silver halide emulsions of which contain more than 90 mol. % of AgCl and less than 0.8 g of silver halide per m² (stated as the equivalent quantity of AgNO₃), characterised in that at least one compound of the formulae (I), (II) or (III) is used as the developer substance:

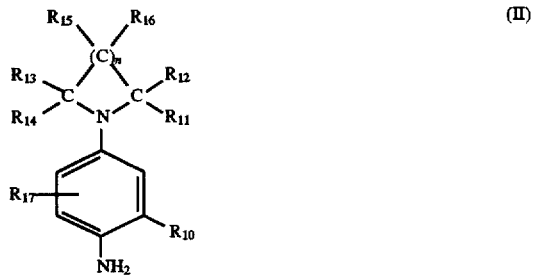

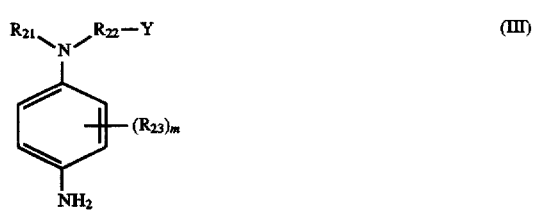

in which $R_1$ and $R_3$ mutually independently mean $C_1-C_4$ alkyl or $R_2$-OH, $R_2$ means $C_1-C_4$ alkylene, $R_{10}$ to $R_{17}$ mutually independently mean hydrogen, $C_1-C_4$ alkyl, OH, COOH, $SO_3H$, $PO_3H_2$, halogen, alkoxy, acylamino, carbamoyl, sulphamoyl, alkoxycarbonyl, acyl, ureido, sulphonyl, sulphamoylamino, alkoxy-carbonylamino, acylaminosulphonyl or sulphonylaminocarbonyl, m means 0, 1 or 2, preferably 1, n means 2, 3 or 4, $R_{21}$ means $C_1-C_6$ alkyl or $R_{22}$-Y, $R_{22}$ means $C_2-C_8$ alkylene, $R_{23}$ means hydrogen, $C_1-C_4$ alkyl, $C_1-C_4$ alkoxy or halogen and Y means $SO_3H$ or COOH, wherein
two or more residues $R_{15}$ or $R_{16}$ may be identical or different and at least one residue $R_{10}$ to $R_{17}$ is not hydrogen and wherein the total concentration of compounds of the formula (I), (II) and (III) in the developer solution is 0.002 to 0.04 mol/l.

Alkyl residues $R_1$, $R_3$, $R_{10}$ to $R_{17}$, $R_{21}$ and $R_{23}$ may be linear or branched.

Alkyl residues $R_{10}$ to $R_{17}$ may themselves be substituted, preferably by $C_1-C_4$ alkoxy, OH, $SO_3H$, COOH, acylamino, carbamoyl, sulphonyl, sulphonamido, sulphamoyl, ureido, alkoxycarbonyl or acyl.

The following meanings preferably apply:

$R_{10}$ is $C_1-C_3$ alkyl, halogen, alkoxy;

$R_3$ is methyl or ethyl;

$R_{17}$ is H.

At least one of the residues $R_{11}$ to $R_{16}$ is OH, COOH, $SO_3H$, acylaminosulphonyl or sulphonylaminocarbonyl.

The compounds of the formulae (I) to (III) may be used as free bases, but are preferably used as salts of inorganic or organic acids, for example as salts of HCl, $H_2SO_4$, oxalic acid and p-toluenesulphonic acid.

The compounds of the formulae (I), (II) and (III) are preferably used in an aqueous solution at a total concentration of 0.005 to 0.035 mol/l.

Examples of compounds of the formulae (I), (II) and (III) are:

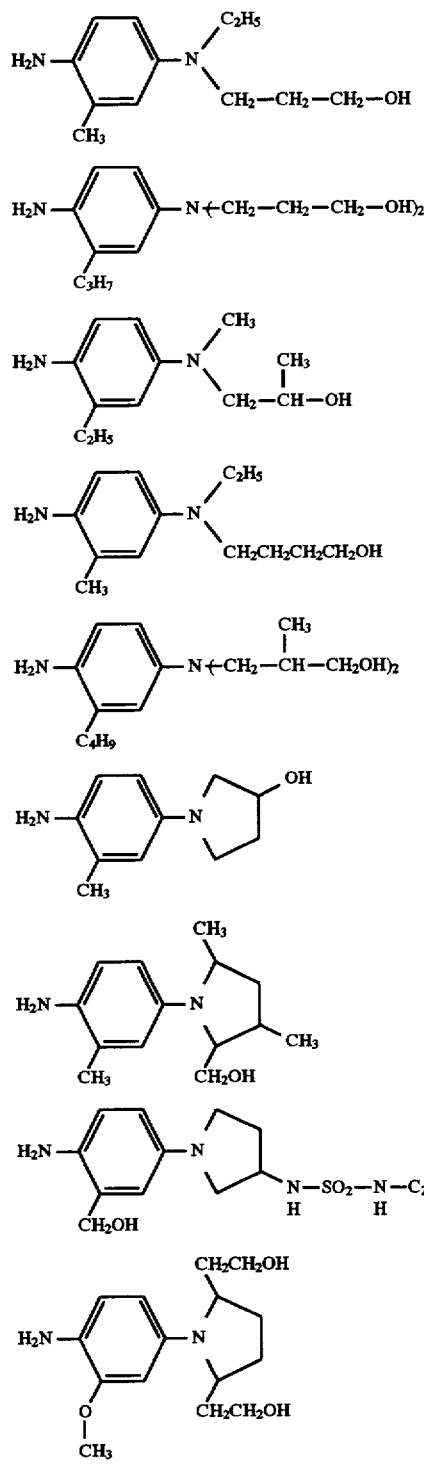

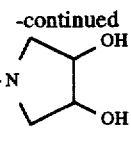

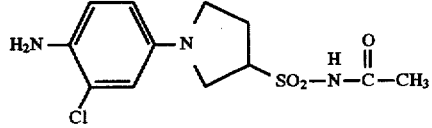

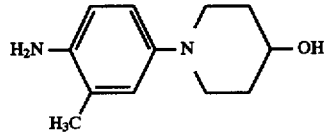

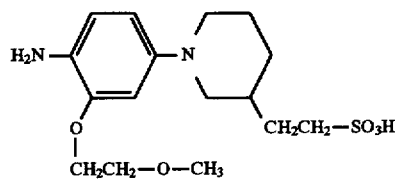

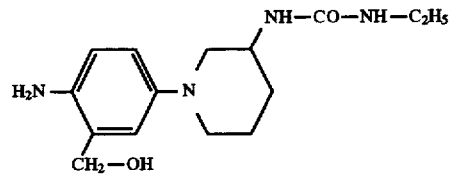

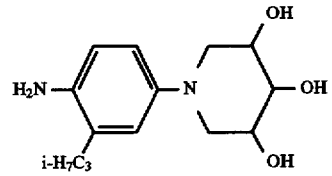

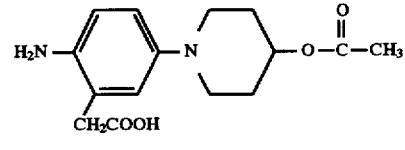

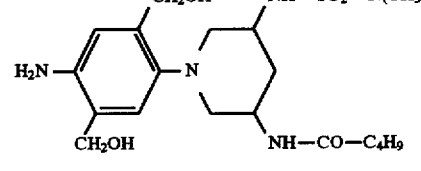

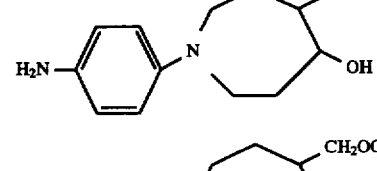

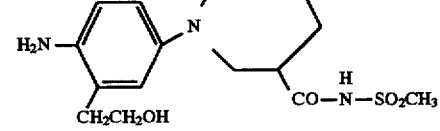

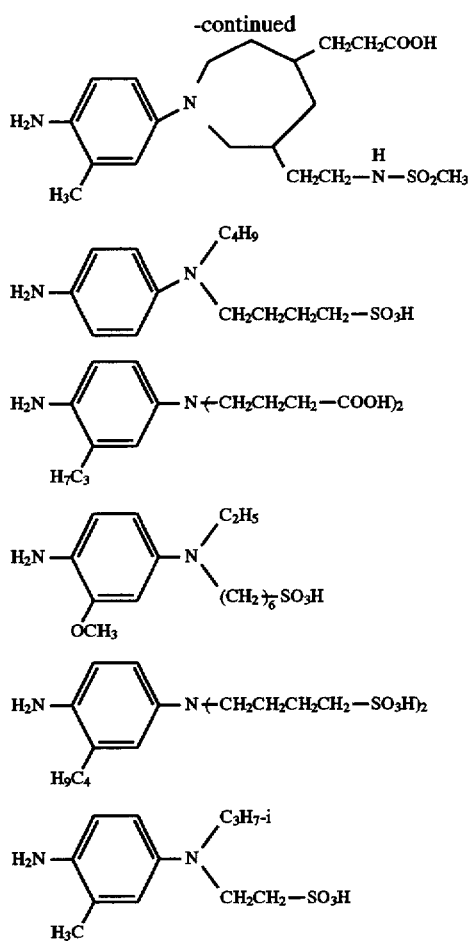

The process according to the invention may be performed as a monobath or two bath process. In both cases, $H_2O_2$ or an $H_2O_2$ releasing compound is used at a concentration of 0.002 to 0.3, preferably of 0.008 to 0.2, particularly preferably of 0.01 to 0.1 mol/l. The complete process in particular includes the following stages:

(a) exposure,
(b) development with a colour developer,
(c) treatment with $H_2O_2$ or a compound which liberates $H_2O_2$,
(d) bleaching and fixing or bleach/fixing or fixing without fixing or stabilisation
(e) optionally rinsing and
(f) drying, wherein stages (b) and (c) may be combined into a single stage and wherein the colour photographic silver halide material contains on a support at least one blue-sensitive silver halide emulsion layer containing at least one yellow coupler, at least one green-sensitive silver halide emulsion layer containing at least one magenta coupler and at least one red-sensitive silver halide emulsion layer containing at least one cyan coupler together with non-photosensitive interlayers between the photosensitive silver halide emulsion layers of differing spectral sensitisation.

The material may moreover contain a substrate layer, further interlayers, one or more yellow filter layers and one or more protective or overcoat layers.

Examples of colour photographic materials are colour negative films, colour reversal films, colour positive films, colour photographic paper, colour reversal photographic paper, colour sensitive materials for the dye diffusion transfer process or the silver dye bleaching process.

Photographic materials consist of a support onto which at least one photosensitive silver halide emulsion layer is applied. Suitable supports are in particular thin films and sheets. A review of support materials and of the auxiliary layers applied to the front and reverse thereof is given in *Research Disclosure* 37254, part 1 (1995), page 285.

Colour photographic materials conventionally contain at least one red-sensitive, one green-sensitive and one blue-sensitive silver halide emulsion layer optionally together with interlayers and protective layers.

Depending upon the nature of the photographic material, these layers may be differently arranged. This is described for the most important products:

Colour photographic films such as colour negative films and colour reversal film have on the support, in the stated sequence, 2 or 3 red-sensitive, cyan-coupling silver halide emulsion layers, 2 or 3 green-sensitive, magenta-coupling silver halide emulsion layers and 2 or 3 blue-sensitive yellow-coupling silver halide emulsion layers. The layers of identical spectral sensitivity differ with regard to their photographic sensitivity, wherein the lower sensitivity partial layers are generally arranged closer to the support than the higher sensitivity partial layers.

A yellow filter layer is conventionally arranged between the green-sensitive and blue-sensitive layers, which filter layer prevents blue light from penetrating the underlying layers.

Colour photographic paper, which is generally substantially less photosensitive than a colour photographic film, conventionally has on the support, in the stated sequence, one blue-sensitive, yellow-coupling silver halide emulsion layer, one green-sensitive, magenta-coupling silver halide emulsion layers and one red-sensitive, cyan-coupling silver halide emulsion layer; the yellow filter layer may be omitted.

The number and arrangement of the photosensitive layers may be varied in order to achieve specific results. For example, all high sensitivity layers may be grouped together in one package of layers and all low sensitivity layers may be grouped together in another package of layers in order to increase sensitivity (DE-A 2 530 645).

Possible options for different layer arrangements and the effects thereof on photographic properties are described in *J. Int. Rec. Mats.*, 1994, volume 22, pages 183–193.

The substantial constituents of the photographic emulsion layers are binder, silver halide grains and colour couplers.

Details of suitable binders may be found in *Research Disclosure* 37254, part 2 (1995), page 286.

Details of suitable silver halide emulsions, the production, ripening, stabilisation and spectral sensitisation thereof, including suitable spectral sensitisers, may be found in *Research Disclosure* 37254, part 3 (1995), page 286 and in *Research Disclosure* 37038, part XV (1995), page 89.

Details relating to colour couplers may be found in *Research Disclosure* 37254, part 4 (1995), page 288 and in *Research Disclosure* 37038, part II (1995), page 80. The maximum absorption of the dyes formed from the couplers and the developer oxidation product is preferably within the following ranges: yellow coupler 430 to 460 nm, magenta coupler 540 to 560 nm, cyan coupler 630 to 700 nm.

In order to improve sensitivity, grain, sharpness and colour separation in colour photographic films, compounds are frequently used which, on reaction with the developer oxidation product, release photographically active compounds, for example DIR couplers which eliminate a development inhibitor.

Details relating to such compounds, in particular couplers, may be found in *Research Disclosure* 37254, part 5 (1995), page 290 and in *Research Disclosure* 37038, part XIV (1995), page 86.

Colour couplers, which are usually hydrophobic, as well as other hydrophobic constituents of the layers, are conventionally dissolved or dispersed in high-boiling organic solvents. These solutions or dispersions are then emulsified into an aqueous binder solution (conventionally a gelatine solution) and, once the layers have dried, are present as free droplets (0.05 to 0.8 μm in diameter) in the layers.

Suitable high-boiling organic solvents, methods for the introduction thereof into the layers of a photographic material and further methods for introducing chemical compounds into photographic layers may be found in *Research Disclosure* 37254, part 6 (1995), page 292.

The non-photosensitive interlayers generally located between layers of different spectral sensitivity may contain agents which prevent an undesirable diffusion of developer oxidation products from one photosensitive layer into another photosensitive layer with a different spectral sensitisation.

Suitable compounds (white couplers, scavengers or DOP scavengers) may be found in *Research Disclosure* 37254, part 7 (1995), page 292 and in *Research Disclosure* 37038, part III (1995), page 84.

The photographic material may also contain UV light absorbing compounds, optical whiteners, spacers, filter dyes, formalin scavengers, light stabilisers, anti-oxidants, $D_{min}$ dyes, additives to improve stabilisation of dyes, couplers and whites and to reduce colour fogging, plasticisers (latices), biocides and others.

Suitable compounds may be found in *Research Disclosure* 37254, part 8 (1995), page 292 and in *Research Disclosure* 37038, parts IV, V, VI, VII, X, XI and XIII (1995), pages 84 et seq.

The layers of colour photographic materials are conventionally hardened, i.e. the binder used, preferably gelatine, is crosslinked by appropriate chemical methods.

Suitable hardener substances may be found in *Research Disclosure* 37254, part 9 (1995), page 294 and in *Research Disclosure* 37038, part XII (1995), page 86.

The silver halides of all the photosensitive layers preferably contain 95 to 100 mol. % of chloride, 0 to 5 mol. % of bromide and 0 to 1 mol. % of iodide. The silver halide emulsions are preferably negative-working emulsions.

EXAMPLE 1

Four multilayer photographic recording materials were produced by applying the following layers in the stated sequence onto paper coated on both sides with polyethylene. All stated quantities relate to 1 m², the quantity of silver is stated as $AgNO_3$.

Material 1

1st Layer (Substrate Layer)
0.10 g of gelatine
2nd Layer (Blue-sensitive Layer)
Blue-sensitive silver halide emulsion (99.5 mol. % of chloride and 0.5 mol. % of bromide, average grain diameter 0.9 μm) prepared from
0.50 g of $AgNO_3$ and
1.25 g of gelatine
0.42 g of yellow coupler Y-1
0.18 g of yellow coupler Y-2
0.50 g of tricresyl phosphate (TCP)
0.10 g of stabiliser ST-1
0.70 mg of blue sensitiser S-1
0.30 mg of stabiliser ST-2

3rd Layer (Interlayer)
1.10 g of gelatine
0.06 g of oxform scavenger O-1
0.06 g of oxform scavenger O-2
0.12 g of TCP
4th Layer (Green-sensitive Layer)
Green-sensitised silver halide emulsion (99.5 mol. % of chloride, 0.5 mol. % of bromide, average grain diameter 0.47 μm) prepared from
0.40 g of $AgNO_3$ and
0.77 g of gelatine
0.41 g of magenta coupler M-1
0.06 g of stabiliser ST-3
0.12 g of oxform scavenger O-2
0.34 g of dibutyl phthalate (DBP)
0.70 mg of green sensitiser S-2
0.50 mg of stabiliser ST-4
5th Layer (UV Protective Layer)
1.15 g of gelatine
0.50 g of UV absorber UV-1
0.10 g of UV absorber UV-2
0.03 g of oxform scavenger O-1
0.03 g of oxform scavenger O-2
0.35 g of TCP
6th Layer (Red-sensitive Layer)
Red-sensitised silver halide emulsion (99.5 mol. % of chloride, 0.5 mol. % of bromide, average grain diameter 0.5 μm) prepared from
0.30 g of $AgNO_3$ and
1.00 g of gelatine
0.46 g of cyan coupler C-1
0.46 g of TCP
0.03 mg of red sensitiser S-3
0.60 mg of stabiliser ST-5
7th Layer (UV Protective Layer)
0.35 g of gelatine
0.15 g of UV absorber UV-1
0.03 g of UV absorber UV-2
0.09 g of TCP
8th Layer (Protective Layer)
0.90 g of gelatine
0.05 g of optical whitener W-1
0.07 g of polyvinylpyrrolidone
1.20 g of silicone oil
2.50 mg of spacer (polymethyl methacrylate)
0.30 g of hardener H-1

Material 2

As material 1, with the following differences:
2nd layer (blue-sensitive layer) with 0.25 g of $AgNO_3$
4th layer (green-sensitive layer) with 0.20 g of $AgNO_3$
6th layer (red-sensitive layer) with 0.15 g of $AgNO_3$ Material 3

1st Layer (Substrate Layer)
2nd Layer (Blue-sensitive Layer)
Blue-sensitive silver halide emulsion (99.5 mol. % of chloride and 0.5 mol. % of bromide, average grain diameter 0.85 μm) prepared from 0.40 g of AgNO$_3$ and
1.36 g of gelatine
0.79 g of yellow coupler Y-3
0.13 g of tricresyl phosphate (TCP)
2.1 –10$^{-4}$ mol of blue sensitiser S-4/mol of AgNO$_3$
2.1 –10$^{-4}$ mol of blue sensitiser S-1/mol of AgNO$_3$
0.04 g of stabiliser ST-6
3rd Layer (Interlayer)
0.7 g of gelatine
0.04 g of oxform scavenger O-1
0.18 g of coupler solvent OF-2
0.18 g of coupler solvent OF-3
0.02 g of stabiliser ST-6
4th Layer (Green-sensitive Layer)
Green-sensitised silver halide emulsion (99.5 mol. % of chloride, 0.5 mol. % of bromide, average grain diameter 0.50 μm) prepared from
0.17 g of AgNO$_3$ and
1.45 g of gelatine
0.16 g of magenta coupler M-2
0.03 g of stabiliser ST-6
0.07 g of stabiliser ST-7
0.50 g of TCP
0.30 g of DBP
5.0 –10$^{-4}$ mol of green sensitiser S-5/mol of AgNO$_3$
3.0 –10$^{-4}$ mol of green sensitiser S-6/mol of AgNO$_3$
5th Layer (UV Protective Layer)
0.70 g of gelatine
0.30 g of UV absorber UV-5
0.20 g of UV absorber UV-3
0.04 g of oxform scavenger O-1
0.36 g of DBP
6th Layer (Red-sensitive Layer)

Red-sensitised silver halide emulsion (99.5 mol. % of chloride, 0.5 mol. % of bromide, average grain diameter 0.50 μm) prepared from
0.31 g of AgNO$_3$ and
1.00 g of gelatine
0.23 g of cyan coupler C-2
0.20 g of cyan coupler C-3
0.30 g of DBP
1.0 –10$^{-4}$ mol of red sensitiser S-7/mol of AgNO$_3$
0.1 g of coupler solvent OF-1
0.04 g of UV absorber UV-3
0.06 g of UV absorber UV-4
0.04 g of UV absorber UV-6
7th Layer (UV Protective Layer)
0.85 g of gelatine
0.12 g of UV-3
0.20 g of DBP
0.24 g of UV-4
0.12 g of UV-6
0.05 g of OF-3
0.05 g of OF-2
8th Layer (Protective Layer)
1.13 g of gelatine
20 mg of paraffin
50 mg of acrylic-modified polyvinyl alcohol copolymer (degree of modification 17%)
Hardener H-2 was added to all layers.

Material 4

As material 3 with the following differences:
b 2nd layer with 0.20 g of AgNO$_3$
4th layer with 0.09 g of AgNO$_3$
6th layer with 0.16 g of AgNO$_3$.

Y-1

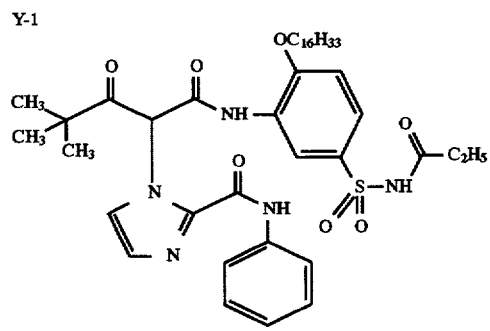

Y-2

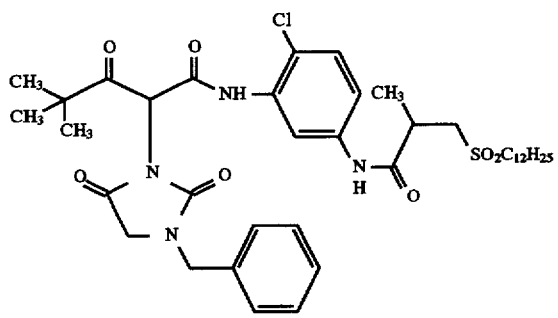

-continued
M-1
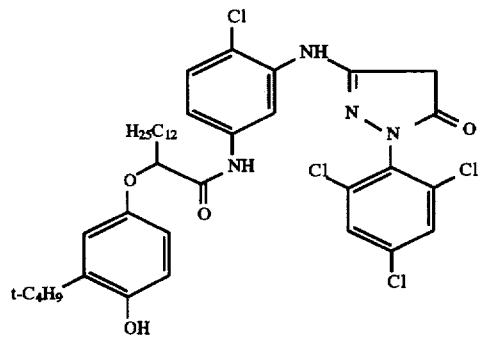
C-1
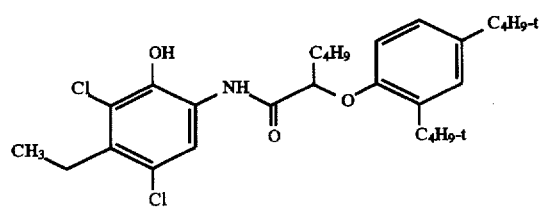
S-1
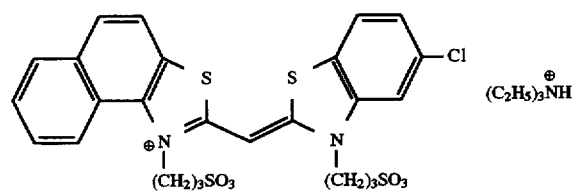
S-2
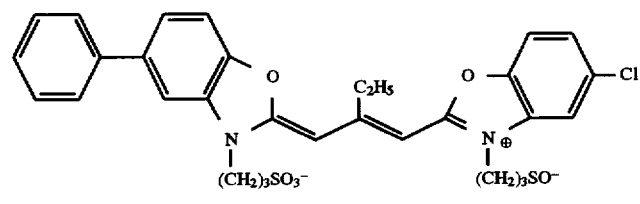
S-3
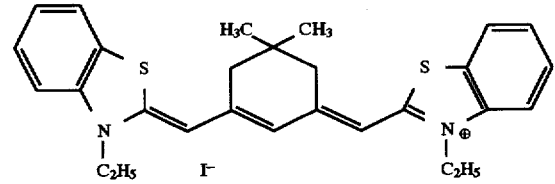
ST-1
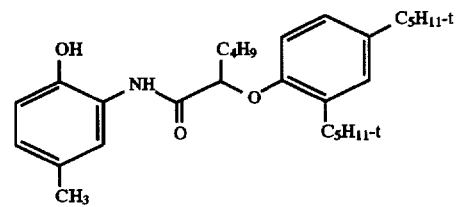

-continued
ST-2
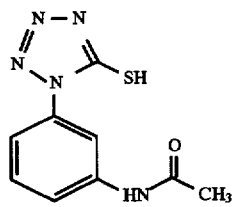
ST-3
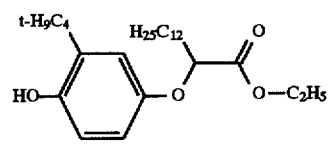
ST-4
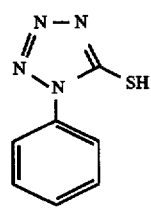
ST-5
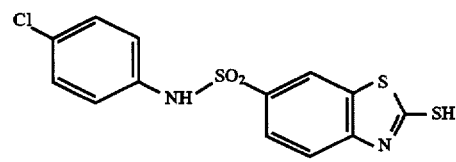
O-1
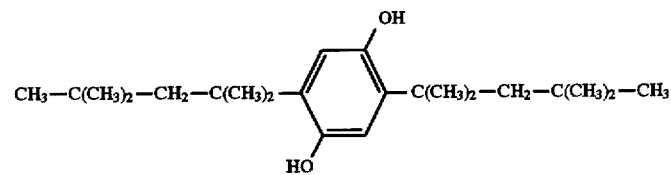
O-2
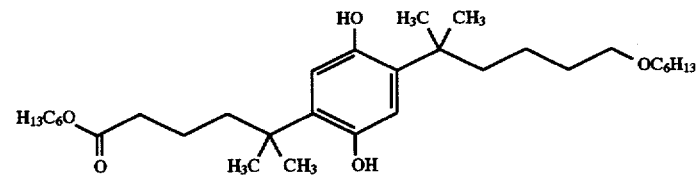
UV-1
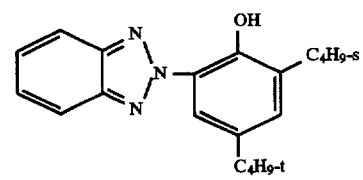

-continued
UV-2
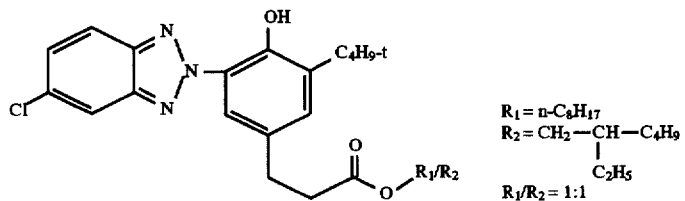
H-1
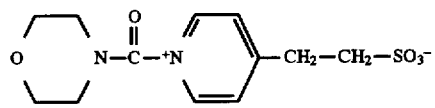
W-1
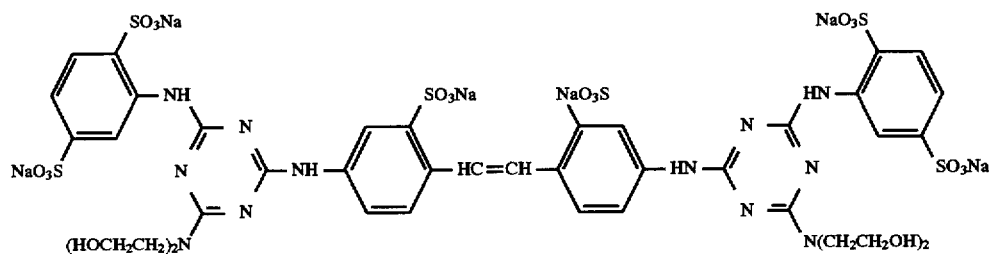
Y-3
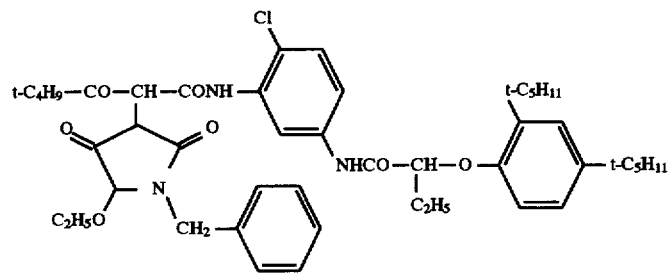
M-2
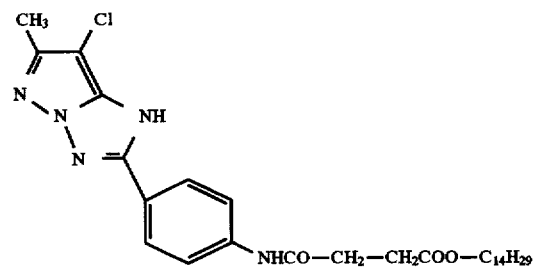
C-3
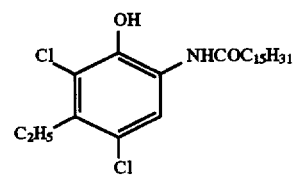

-continued
C-2
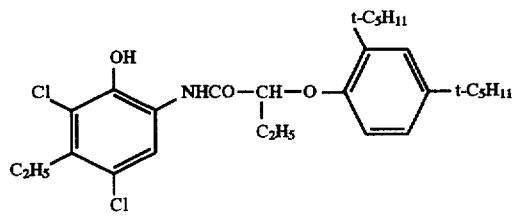
S-4
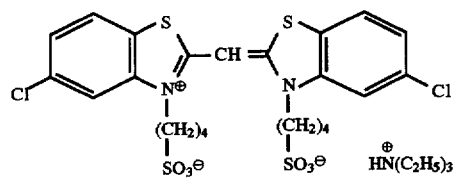
S-5
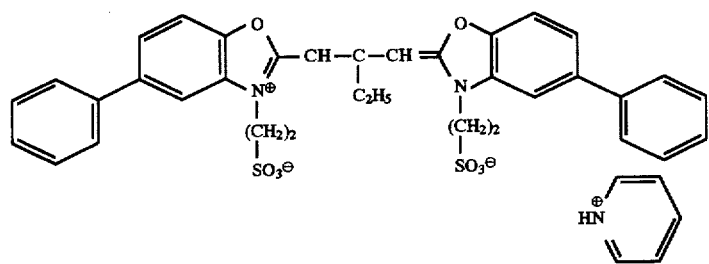
S-6
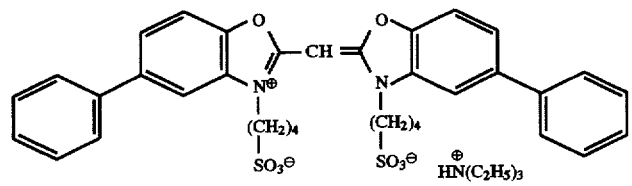
S-7
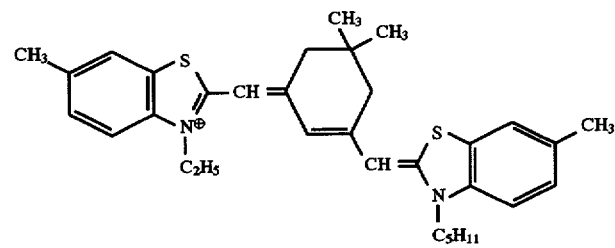
ST-6
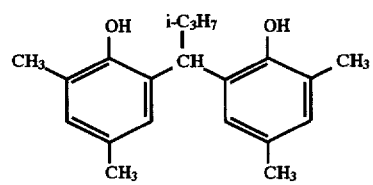

ST-7 1:1:0.2 mixture by weight prepared from a) 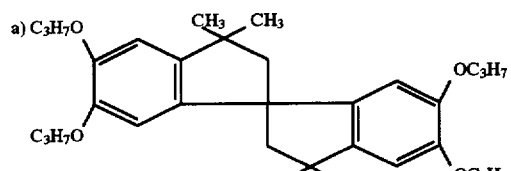

b) 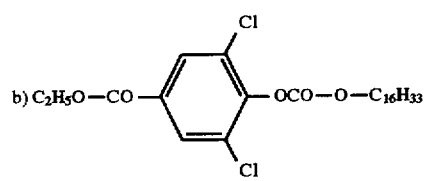

c) 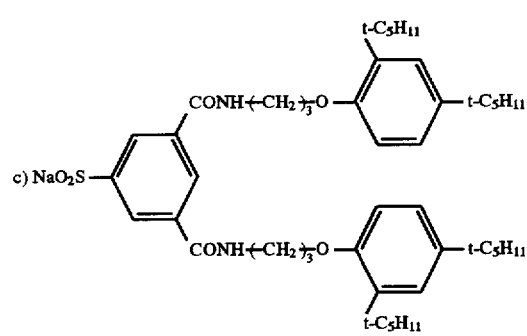

UV-3 Mixture of UV-1 and

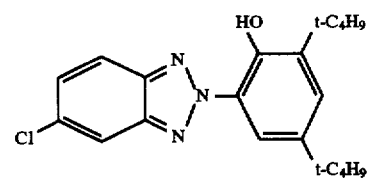

UV-4 Mixture of UV-2, UV-5 and

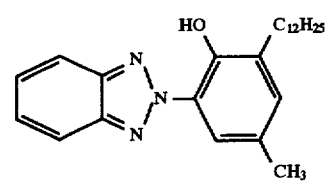

UV-5

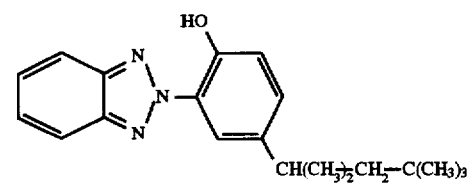

UV-6

H-2 $(CH_2=CH-SO_2-CH_2-CONH-CH_2)_2$

-continued

OF-1 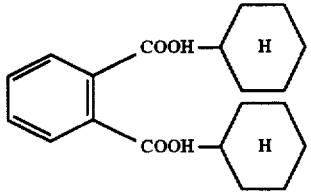

OF-2 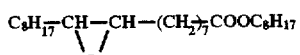

OF-3 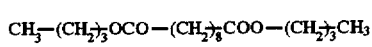

The colour photographic recording materials are exposed behind a step wedge. On exposure, additional filters are placed in the beam path of the exposure unit such that the wedges appear neutral at an optical density of D=0.6. The exposed materials are processed using processes 1 to 5.

Process 1

| Stage | Time | Temperature |
|---|---|---|
| Development | 45 sec | 35° C. |
| Bleach/fixing | 45 sec | 35° C. |
| Rinsing | 90 sec | 33° C. |

The processing baths were prepared in accordance with the following instructions:

Colour Developer Solution

| Tetraethylene glycol | 20.0 g |
|---|---|
| N,N-diethylhydroxyiamine | 4.0 g |
| (N-ethyl-N-(2-methanesulphonamido)ethyl)-4-amino-3-methylbenzene sulphate (CD-3) | 5.0 g |
| Potassium sulphite | 0.2 g |
| Potassium carbonate | 30.0 g |
| Hydroxyethanediphosphonic acid | 0.2 g |
| Optical whitener (4,4'-diaminostilbene-sulphonic acid derivative) | 2.0 g |
| Potassium bromide | 0.02 g | make up to 1 l with water, adjust pH to 10.2 with KOH or $H_2SO_4$.

Bleach/fixing Bath Solution

| Ammonium thiosulphate | 75.0 g |
|---|---|
| Sodium hydrogen sulphite | 13.5 g |
| Ethylenediaminetetraacetic acid (iron/ammonium salt) | 45.0 g | make up to 1 l with water, adjust pH to 6.0 with ammonia (25%) or acetic acid.

Process 2 (Monobath Intensification Process)

| Stage | Time | Temperature |
|---|---|---|
| Development & intensification | 45 sec | 35° C. |

21
-continued

| Stage | Time | Temperature |
|---|---|---|
| Fixing | 45 sec | 35° C. |
| Rinsing | 90 sec | 35° C. |

The processing baths were prepared in accordance with the following instructions:

Colour Intensification Developer Solution

| | |
|---|---|
| Potassium sulphite | 0.5 g |
| Potassium phosphate | 40.0 g |
| Potassium hydrogen phosphate | 6.0 g |
| Hydroxyethanediphosphonic acid | 0.2 g |
| CD-3 | 4.0 g |
| Hydrogen peroxide ($H_2O_2$, 30 wt. %) | 200 ml | make up to 1 l with water, adjust pH to 10.0.

Fixing Bath Solution

| | |
|---|---|
| Ammonium thiosulphate | 150.0 g |
| Sodium sulphite | 10.0 g |
| Sodium hydrogen sulphite | 2.5 g | make up to 1 l with water, adjust pH to 7.0.

Process 3 (Two Bath Intensification Process)

| Stage | Time | Temperature |
|---|---|---|
| Development | 45 sec | 35° C. |
| Intensification | 45 sec | 27° C. |
| Fixing | 45 sec | 35° C. |
| Rinsing | 90 sec | 35° C. |

The processing baths were prepared in accordance with the following instructions:

22
Colour Developer Solution

| | |
|---|---|
| Potassium sulphite | 0.5 g |
| Potassium phosphate | 40.0 g |
| Potassium hydrogen phosphate | 6.0 g |
| Hydroxyethanediphosphonic acid | 0.2 g |
| CD-3 | 6.0 g | make up to 1 l with water, adjust pH to 11.0.

Intensification Bath Solution

| | |
|---|---|
| Hydrogen peroxide ($H_2O_2$, 30%) | 20.0 ml |
| Potassium hydrogen phosphate | 4.5 g |
| Diethylenetriaminepentaacetic acid, penta-sodium salt | 1.0 g |
| pH 8.5 | |

Fixing Bath Solution

| | |
|---|---|
| Ammonium thiosulphate | 150.0 g |
| Sodium sulphite | 10.0 g |
| Sodium hydrogen sulphite | 2.5 g | make up to 1 l with water, adjust pH to 6.0.

Process 4 corresponds to process 2, with 3.0 g of colour developer instead of 4 g of colour developer; pH of developer 11.0.

Process 5 corresponds to process. 3, with 4.5 g of colour developer instead of 6.0 g of colour developer; pH of developer 10.8.

In further tests, CD-3 was replaced with other developer substances: CD-4 (4-amino-3-methyl-N-ethyl-N-β-hydroxyethylaniline sulphate), I-1, II-2, III-5.

The minimum density ($D_{min}$) and maximum density ($D_{max}$) of the samples were measured with a reflected light densitometer. The following values were obtained:

TABLE 1

| | | | | D-min (× 1000) | | | D-max (× 100) | | |
|---|---|---|---|---|---|---|---|---|---|
| Sample | Material | Process | Developer | Yellow | Magenta | Cyan | Yellow | Magenta | Cyan |
| 1 | 1 | 1 | CD-3 | 108 | 117 | 108 | 255 | 255 | 262 |
| 2 | 2 | 1 | CD-3 | 94 | 105 | 95 | 126 | 136 | 124 |
| 3 | 3 | 1 | CD-3 | 106 | 113 | 112 | 210 | 235 | 237 |
| 4 | 4 | 1 | CD-3 | 95 | 102 | 99 | 108 | 115 | 119 |
| 5 | 1 | 2 | CD-3 | 190 | 169 | 122 | 223 | 270 | 265 |
| 6 | 1 | 3 | CD-3 | 142 | 153 | 125 | 264 | 266 | 262 |
| 7 | 2 | 2 | CD-3 | 149 | 145 | 120 | 251 | 264 | 261 |
| 8 | 2 | 3 | CD-3 | 135 | 141 | 120 | 222 | 253 | 250 |
| 9 | 3 | 2 | CD-3 | 233 | 214 | 175 | 182 | 260 | 279 |
| 10 | 3 | 3 | CD-3 | 158 | 178 | 165 | 250 | 260 | 271 |
| 11 | 4 | 2 | CD-3 | 143 | 129 | 120 | 254 | 258 | 262 |
| 12 | 4 | 3 | CD-3 | 133 | 131 | 122 | 224 | 247 | 252 |
| 13 | 2 | 2 | CD-4 | 137 | 128 | 134 | 247 | 260 | 262 |
| 14 | 2 | 2 | I-1 | 132 | 124 | 130 | 243 | 255 | 259 |
| 15 | 2 | 2 | II-2 | 134 | 126 | 127 | 241 | 250 | 256 |
| 16 | 2 | 2 | III-5 | 139 | 135 | 138 | 241 | 254 | 263 |
| 17 | 2 | 3 | CD-4 | 136 | 133 | 132 | 238 | 250 | 252 |
| 18 | 2 | 3 | I-1 | 134 | 137 | 134 | 239 | 242 | 255 |
| 19 | 2 | 3 | II-2 | 133 | 135 | 133 | 236 | 242 | 253 |
| 20 | 2 | 3 | III-5 | 126 | 124 | 124 | 237 | 240 | 256 |
| 21 | 4 | 2 | CD-4 | 140 | 137 | 125 | 239 | 256 | 262 |
| 22 | 4 | 2 | I-1 | 145 | 134 | 127 | 237 | 249 | 253 |
| 23 | 4 | 2 | II-2 | 146 | 130 | 124 | 236 | 249 | 257 |

TABLE 1-continued

| | | | | D-min (× 1000) | | | D-max (× 100) | | |
|---|---|---|---|---|---|---|---|---|---|
| Sample | Material | Process | Developer | Yellow | Magenta | Cyan | Yellow | Magenta | Cyan |
| 24 | 4 | 2 | III-5 | 142 | 132 | 126 | 245 | 253 | 259 |
| 25 | 4 | 3 | CD-4 | 137 | 133 | 132 | 236 | 248 | 255 |
| 26 | 4 | 3 | I-1 | 134 | 130 | 133 | 235 | 246 | 252 |
| 27 | 4 | 3 | II-2 | 135 | 134 | 135 | 238 | 250 | 251 |
| 28 | 4 | 3 | III-5 | 129 | 123 | 122 | 239 | 246 | 255 |
| 29 | 2 | 4 | CD-4 | 125 | 123 | 122 | 238 | 247 | 250 |
| 30 | 2 | 4 | I-1 | 124 | 121 | 124 | 239 | 244 | 249 |
| 31 | 2 | 4 | II-2 | 126 | 123 | 122 | 235 | 242 | 247 |
| 32 | 2 | 4 | III-5 | 124 | 123 | 126 | 239 | 240 | 248 |
| 33 | 4 | 4 | CD-4 | 129 | 124 | 122 | 233 | 241 | 248 |
| 34 | 4 | 4 | I-1 | 125 | 123 | 120 | 230 | 243 | 244 |
| 35 | 4 | 4 | II-2 | 126 | 123 | 123 | 234 | 240 | 248 |
| 36 | 4 | 4 | III-5 | 123 | 125 | 124 | 234 | 242 | 249 |
| 37 | 2 | 5 | CD-4 | 124 | 122 | 118 | 233 | 241 | 248 |
| 38 | 2 | 5 | I-1 | 125 | 123 | 119 | 230 | 240 | 248 |
| 39 | 2 | 5 | II-2 | 126 | 120 | 122 | 231 | 244 | 249 |
| 40 | 2 | 5 | III-5 | 124 | 121 | 120 | 233 | 245 | 246 |
| 41 | 4 | 5 | CD-4 | 123 | 121 | 118 | 231 | 244 | 246 |
| 42 | 4 | 5 | I-1 | 126 | 119 | 119 | 233 | 240 | 244 |
| 43 | 4 | 5 | II-2 | 125 | 118 | 120 | 234 | 242 | 247 |
| 44 | 4 | 5 | III-5 | 124 | 122 | 118 | 233 | 241 | 243 |

Samples 1 to 28 are comparative samples.

Samples 1 and 3 show the results with conventional materials using normal processing without intensification. A reduction in the quantity of silver halide (samples 2 and 4) gives rise to unacceptable results.

The monobath intensification process with CD-3 as the developer substance results in excessively high fog values ($D_{min}$) (samples 5, 7, 9 and 11); the same applies to the two bath intensification process; furthermore in some cases yellow densities are inadequate (samples 6, 8, 10, 12).

Materials with a reduced silver content, processed using the monobath and two bath process with conventional quantities of developer also give rise to high $D_{min}$ values (samples 13 to 28).

It is only the combination of materials having a low silver content and development intensification processing with development baths having a particularly low developer content and containing developers according to the invention which gives rise to adequate maximum densities accompanied by low fog (samples 29 to 44).

EXAMPLE 2

After processing, the samples stated in table 1 were exposed to the light from a daylight standardised xenon lamp (100 d.lux) and irradiated with 15 –10⁶ lux –h. The percentage reduction in density at a starting density of D=1.0 was then determined for all three colours (table 2).

TABLE 2

| (C: comparison, I: according to the invention) | | | | |
|---|---|---|---|---|
| | Colour devel- | Percentage reduction in density at starting density D = 1.0 | | |
| Sample | oper | Y | M | C |
| 8 (C) | CD-3 | 19 | 17 | 16 |
| 53 (C) | CD-4 | 28 | 26 | 25 |
| 54 (I) | I-1 | 20 | 17 | 15 |

TABLE 2-continued

| (C: comparison, I: according to the invention) | | | | |
|---|---|---|---|---|
| | Colour devel- | Percentage reduction in density at starting density D = 1.0 | | |
| Sample | oper | Y | M | C |
| 55 (I) | II-2 | 21 | 17 | 14 |
| 56 (I) | III-5 | 22 | 18 | 17 |
| 12 (C) | CD-3 | 13 | 8 | 10 |
| 49 (C) | CD-4 | 28 | 30 | 17 |
| 50 (I) | I-1 | 14 | 8 | 8 |
| 51 (I) | II-2 | 15 | 9 | 10 |
| 52 (I) | III5 | 15 | 8 | 11 |

Y = yellow; M = magenta; C = cyan

As table 2 shows, virtually the same dye stability may be achieved with the colour developers according to the invention as with CD-3, in contrast with CD-4, which gives rise to substantially reduced stability.

We claim:

1. A development intensification process for processing color photographic silver halide materials, the silver halide emulsions of which contain more than 90 mol-% of AgCl and less than 0.8 g of silver halide per m² (stated as the equivalent quantity of $AgNO_3$), which comprises at least one compound of the formula (II) as the developer substance:

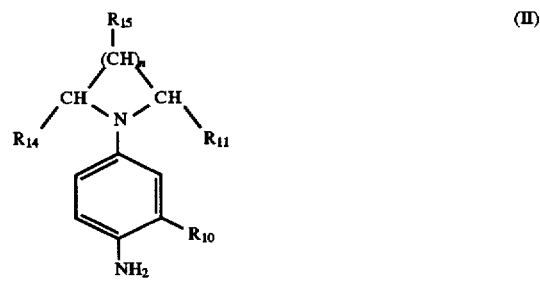

(II)

in which $R_{10}$ means $C_1$–$C_4$ alkyl or alkoxy, $R_{11}$, $R_{14}$, $R_{15}$ mutually independently mean hydrogen, $C_1$–$C_4$ alkyl, OH, COOH, $SO_3H$, alkoxy, sulphamoyl, ureido, acylaminosulphonyl, or sulphonylaminocarbonyl, n means 2 or 3, and wherein the total concentration of compounds of the formula (I) and (II) in the developer solution is 0.002 to 0.04 mol/l.

2. The development intensification process according to claim 1, wherein $R_{10}$ means $C_1$–$C_3$ alkyl, at least one of the residues $R_{11}$, $R_{14}$ and $R_{15}$ means OH, COOH, $SO_3H$, acylaminosulphony or sulphonylaminocarbonyl.

3. The development intensification process according to claim 1, wherein the compounds of the formula (II) are used in aqueous solution at a total concentration of 0.005 to 0.035 mol/l.

4. The development intensification process according to claim 1, wherein the process is performed as a monobath ot two bath process.

5. The development intensification process according to claim 4, wherein the monobath or two bath process uses $H_2O_2$ or an $H_2O_2$ releasing compound at a concentration from 0.002 to 0.3 mol/l.

6. The development intensification process according to claim 4, wherein the monobath or two bath process uses $H_2O_2$ or an $H_2O_2$ releasing compound at a concentration from 0.008 to 0.2.

7. The development intensification process according to claim 4 wherein the monobath or two bath process uses $H_2O_2$ or an $H_2O_2$ releasing compound at a concentration from 0.001 to 0.1 mol/l.

* * * * *